US006639781B2

(12) United States Patent
Smith et al.

(10) Patent No.: US 6,639,781 B2
(45) Date of Patent: Oct. 28, 2003

(54) ELECTROMAGNETIC DENT REMOVER POWER SUPPLY

(75) Inventors: David B. Smith, Renton, WA (US);
Robert F. Olsen, Bothell, WA (US);
John J. Cotter, Long Beach, CA (US)

(73) Assignee: The Boeing Company, Chicago, IL (US)

(*) Notice: Subject to any disclaimer, the term of this patent is extended or adjusted under 35 U.S.C. 154(b) by 35 days.

(21) Appl. No.: 10/001,359

(22) Filed: Oct. 31, 2001

(65) Prior Publication Data
US 2003/0063425 A1 Apr. 3, 2003

Related U.S. Application Data
(60) Provisional application No. 60/326,573, filed on Oct. 31, 2001.

(51) Int. Cl.[7] ............................................. H01H 47/00
(52) U.S. Cl. .................................................... 361/155
(58) Field of Search ................................ 361/143, 156, 361/155, 135

(56) References Cited

U.S. PATENT DOCUMENTS 5,734,256 A * 3/1998 Larsen et al. ............... 323/207

* cited by examiner

Primary Examiner—Gregory J. Toatley, Jr.
(74) Attorney, Agent, or Firm—Black Lowe & Graham PLLC

(57) ABSTRACT

A power supply for an electromagnetic force system comprising a slow current pulse system in parallel with a dumping circuit feeding a blocking inductor in parallel with a series of diodes; a fast current pulse system of opposing polarity and parallel to the slow current pulse system and blocking inductor, the fast pulse system including a triggered vacuum spark-gap for discharging the fast current pulse system through a working coil such that the current through the coil decreases rapidly and the magnetic field in the gap decreases substantially while the magnetic field in and behind the work piece decreases only slightly, resulting in a large field gradient across the work piece and the creation of a pulse of tension force on the work piece.

8 Claims, 5 Drawing Sheets

ELECTROMAGNETIC DENT REMOVER POWER SUPPLY

RELATED APPLICATIONS

This application claims priority from provisional application No. 60/326,573 filed on Oct. 31, 2001.

FIELD OF THE INVENTION

This invention is directed to electromagnetic force machines and, more particularly, to electromagnetic force machines suitable for performing non-destructive tests on or removing dents from a panel.

BACKGROUND OF THE INVENTION

In the past, a variety of electromagnetic force (EMF) machines have been developed for use in the production and maintenance of panels to perform non-destructive tests on panel bonds and to remove dents. U.S. Pat. No. 4,148,091 issued to Karl A. Hansen et al on Apr. 3, 1979 entitled "Electromagnetic force machine with universal portable power supply," and U.S. Pat. No. 3,825,819 issued to Karl A. Hansen et al on Jul. 23, 1974 entitled "Dynamic Proof Loading of Metal Bond Structures Using Pulsed Magnetic Fields" describe such a machine. U.S. Pat. No. 5,046,345 issued to Peter B. Zieve on Sep. 10, 1991 entitled "Power Supply for Electromagnetic Proof Load Tester and Dent Remover" teaches the power supply for such dent pullers.

Aircraft mechanics commonly use electromagnetic energy to produce a pulling (tension) force in electrically conducting members such as aircraft metal skin panels. Controlling the current through a working-coil generates magnetic fields in metal skin panels. A magnetic field with the capability of drawing the dent from a work piece must extend across a gap between a working-coil through the adjacent work piece and extending behind. The field induces a current and a corresponding magnetic field within the conductive work piece. Rapid changes in the magnetic field impart forces on induced current within the work piece. The pulling force is local and works to repair dents. The current in the coil is the result of a series of charge pulses under voltage. The discharge of capacitors creates these pulses To set the stage for dent pulling, chargers charge both fast- and slow-banks of capacitors. When each bank is fully charged, a trigger closes an SCR allowing the slow-bank capacitors to discharge a large current at a relatively low voltage (less than 1000 volts). The discharged current flows through a blocking inductor that smoothes the pulse in a manner to produce a slow rising current pulse. This pulse continues through a work coil positioned adjacent the dented area of the panel.

Current in the working-coils produces corresponding magnetic fields. The current through the work coil creates a magnetic field in and immediately behind the work piece, and in the gap between the coil and the work piece. When the slow current pulse has reached its peak amplitude, approximately 2 milliseconds from initial discharge, a timing pulse to a spark-gap discharges the fast-capacitor bank. The spark-gap releases a current pulse at a high voltage (approximately 2–15 kV) in the opposite direction through the working-coil. The fast-capacitor bank fires on the blocking inductor and working-coil in parallel to produce a fast rising current pulse opposite in polarity to the slow pulse.

The fast-capacitor bank discharge decreases the current through the coil. The current flow in the working-coil quickly diminishes the current in about 10–30 μSec. (Times reflect a normal application and not the functional range.) The magnetic field in the gap between the coil and the work piece quickly is diminished. The difference in the magnetic fields in and behind the work piece as compared to that in the gap produces a Lorentz force. That force pushes the depressed, dented, area outward.

The timing of the fast-capacitor bank discharge in relation to the slow-capacitor bank discharge determines the result. The interplay of the pulses creates a precise set of magnetic field states within the work piece resulting in the force that pulls the dent. That interplay of pulses depends upon the unfailing performance of the gas-filled spark-gap.

Gas-filled spark-gaps do fail. The hold-off voltage of the device falls very slowly during life until it reaches a critical point from which it falls very rapidly; this is due to the deposit of a metallic coating on the internal insulator surface separating the electrodes. High voltage, high current sparking heats conduction spots on the surface of the electrodes. The metallic coating is re-deposited metal, vaporized and eroded from the electrodes.

The lifetime of a gas-filled spark gap is a function of the number of firings, the charge transfer per firing, and the peak current through the spark gap on each firing. The gas-filled spark-gaps tend to fail in two catastrophic modes, leading to, alternately, prefires and misfires. Prefires may occur without a triggering pulse. A prefire discharge occurs when the applied DC voltage is greater than the resulting hold-off voltage caused by the deterioration of the spark gap. A misfire, on the other hand, is a failure of the tube to break down with the triggering pulse.

A misfire results in non-performance by the electronic dent removing apparatus; a prefire, the application of a rapid unplanned tension force on the work piece without the countervailing slow pulse magnetic field. The prefire of the fast-capacitor bank yields a very sharp pulse that dents the work piece. The leverage of the machine to create a dent is greater than its ability to pull them out. The prefire causes a very severe dent and often results in the need for the removal and replacement of the skin panel.

Because of the sudden, unpredictable, and catastrophic results from failure of gas-filled spark-gaps in electronic dent remover power supplies, there is an unmet need in the art for a means to predictably discharge the fast-bank capacitors. Such predictable discharges would remove the risk of the catastrophic effects of prefire discharge of the fast-bank capacitors through the coil.

SUMMARY OF THE INVENTION

The present invention eliminates the several dangers presented by the use of gas-filled triggered spark-gaps to discharge the fast-capacitor bank in an electronic dent remover. The enhanced performance range of the vacuum triggered spark-gap in conjunction with dump circuits across the capacitor banks provides greater safety, reliability, and predictability in operation.

The invention is a power supply for an electromagnetic force system, operating by alternately energizing a working coil with a slow current pulse from a bank of capacitors through a blocking inductor, each capacitor bank connected in parallel with a dumping circuit, for discharging said slow current pulse system through the blocking inductor at a selected time; and then an opposite fast current pulse system, resulting in a large field gradient across the work piece thereby creating a pulse of tension force on the work piece. The clamping circuit across the blocking inductor provides an alternate path for discharging the energy from the blocking inductor, further enhancing the performance of the electronic dent remover.

BRIEF DESCRIPTION OF THE DRAWINGS

The preferred and alternative embodiments of the present invention are described in detail below with reference to the following drawings.

DETAILED DESCRIPTION OF THE INVENTION

Figure 1:
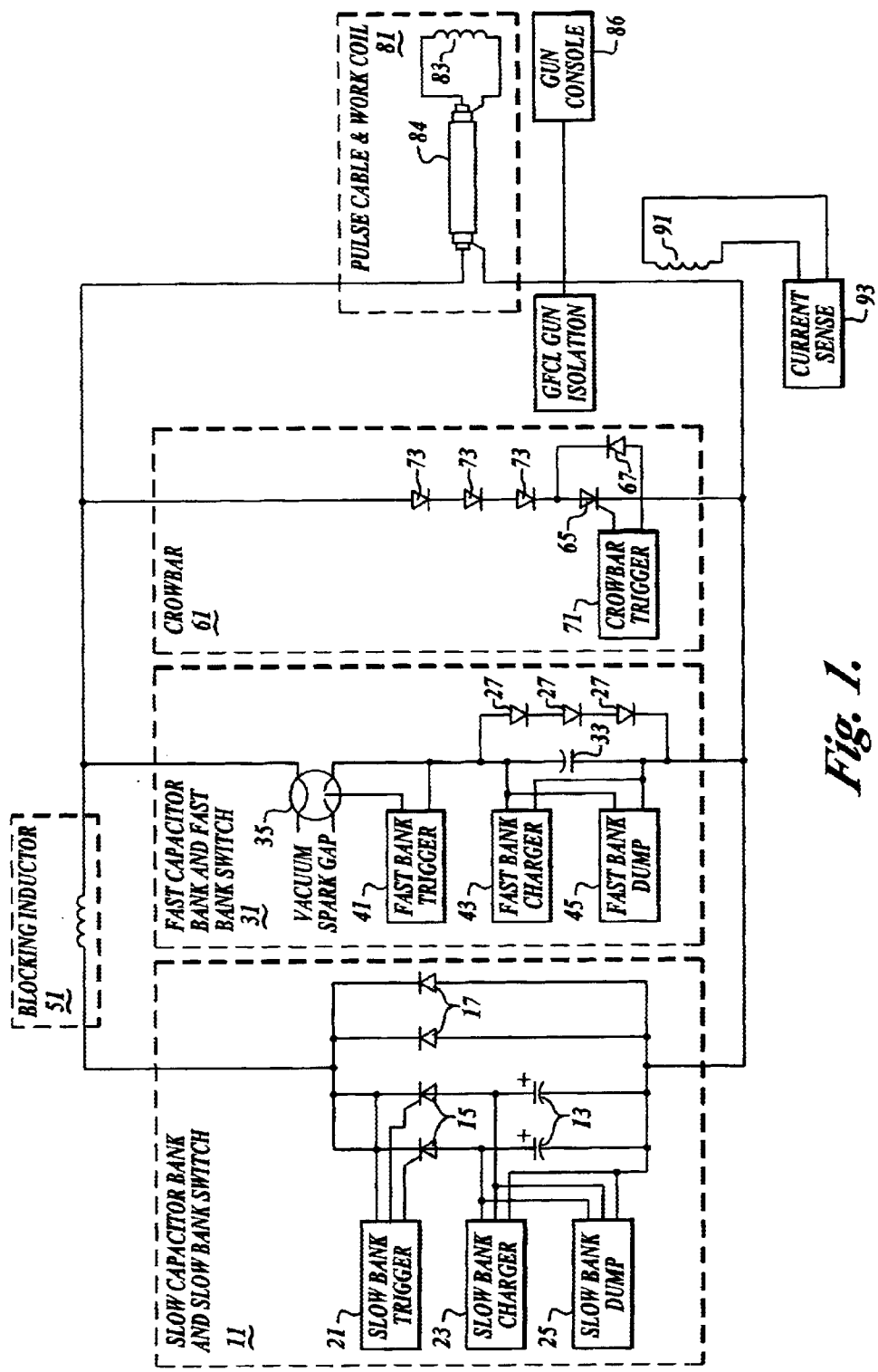
FIG. 1 is a schematic diagram of the invention.

The present invention is an apparatus for supplying power to an electronic dent remover or proof loader. FIG. 1 portrays the inventive power supply. The apparatus comprises seven principal components: a slow-capacitor bank 11 with attendant SCR 15, dump circuit 25, and charger 23; a fast-capacitor bank with attendant triggered vacuum spark-gap 35, dump 45, and charger 45; a blocking inductor 51; the crowbar circuit 61; the working-coil assembly 81; and, the current sensing transformer 91. The details of the triggering circuits and the controlling instrumentation are neither claimed nor portrayed.

The inventive apparatus generates rapidly changing magnetic fields by timed electrical discharges from banks of capacitors into the working-coil 83. Prior to discharge, the two banks, i.e. the slow-bank 13 and the fast-bank 33, of capacitors are appropriately charged. Distinct chargers charge the capacitor banks; the slow-bank charger 23 and the fast-bank charger 43 each act to fully charge the respective banks to their appropriate levels.

To create a magnetic field in the working-coil 83, a timing pulse triggers SCR 15 conductive, allowing the slow-capacitor bank 13 to discharge its stored charge as current through the working-coil 83. The inductive effects of the blocking inductor 51 in series between the slow capacitor bank 13 and the working-coil 83 slow the discharge of current from the slow-capacitor bank 13. The slow building and then decaying current creates a magnetic field as it passes through the working-coil 83 inducing the current in the work piece.

As the current within the working-coil 83 reaches its peak, a triggering pulse sent to the vacuum spark-gap 35 allows the discharge of the fast-capacitor bank 33. Due to the opposing polarity of the voltage across the fast-capacitor bank 33, the discharge decreases the current in the working-coil 83 and increases the current in the blocking coil 51. Rather than allowing the energy to continue to move from coil 83 to coil 51, the diode shunts the current dissipating the energy in the working coil 83. This opposing flow serves to "clamp" the voltage across the coil and will thus prevent oscillations, i.e. ringing, between the coil 83 and the fast- and slow-capacitor banks 33 and 13 respectively. The rapid change in current and the resulting rapid reversal of the magnetic field produces the desired bending of the work piece.

The slow-capacitor bank 13 includes parallel flyback diodes 17. Protective flyback diodes 17 are connected in parallel with the series comprising the slow capacitor bank 13 and the SCR 15. Placement of the flyback diodes 17 protects the switching SCR 15 against an accidental firing of the fast capacitor bank when the SCR 15 are not triggered conductive. In the event of an accidental firing of the fast-capacitor bank, current from the discharge will flow through the flyback diodes 17 around the SCR 15 and the slow-capacitor bank 13. Doing so also assures predictable reliable triggering of the SCR 15, by releasing residual charge at the common node.

The slow-capacitor bank 13 has many of the features of the fast-capacitor bank 33. The inventive circuit places a dump circuit 25 in parallel to a slow-capacitor bank 13 in series with a triggering SCR 15 and a charger 23. The dump circuit 25 allows the safe discharge of the slow-capacitor bank 13 when avoiding discharge through the working-coil 83. A dump circuit 45 parallel to a fast-capacitor bank 33 and a charger 43 provide the same safe discharge path for the fast-capacitor bank 33.

A crowbar circuit 61 provides a short circuit across the work coil allowing further clamping of the voltage. An SCR 65 in series with the crowbar circuit 61 opens and closes the short circuit with precise timing. A plurality of diodes 73 stand in series with the SCR 65 to block large reverse voltages and to pass current through the crowbar when the SCR 65 is triggered conductive. Closed, the short circuit "clamps" the voltage in the circuit. This clamping prevents the increase of current in the working coil 83.

A flyback diode 67, serves to protect the SCR 65, and to assure its reliable operation. The flyback diode 67 assures the shunting of the large reverse bias caused by the discharge of fast-capacitor bank 33, reducing the stress on the SCR 65.

A pickup transformer 91 produces a current indicative of the magnitude of the working-coil current. A transducer 93 senses the current and reports the same to instrumentation that controls the triggering of the SCRs 15 and 65 and the triggered vacuum spark-gap 35. If, at the time of slow-capacitor bank firing, the instrumentation senses that the current is not large enough, it disables the firing of the fast-bank firing circuit. By doing so when the slow bank current is small, the discharge of the fast-capacitor bank does not present its large unbalanced current to the working-coil 83, averting application of an overly large magnetic force so preventing further damage to the work piece.

The inventive apparatus differs from the prior art in several important details. These details prevent catastrophic prefiring of the fast-capacitor bank. The first of these details is the use of a triggered vacuum spark-gap 35. The triggered vacuum spark-gap 35 comprises an evacuated chamber with three electrodes. Two of the three electrodes are endplates for passing the charge across the gap and the third electrode serves to trigger the device by initiating a spark. The gas-filled spark-gap, used in the prior art, differs from the vacuum gap in that it uses a field pressured with inert gases.

A triggered vacuum gap 35 has very distinct operating characteristics to the gas-filled spark-gap. These characteristics include a generally broader operating range and a generally greater self-breakdown voltage. The vacuum spark-gap 35 is not as susceptible to prefiring, as its design presumes the redistribution of metal ions from and to its electrodes. The principal failure mode becomes misfiring due to the erosion of the electrodes. The change of parameters eliminates the more dangerous prefiring as a failure mode.

Figure 2:
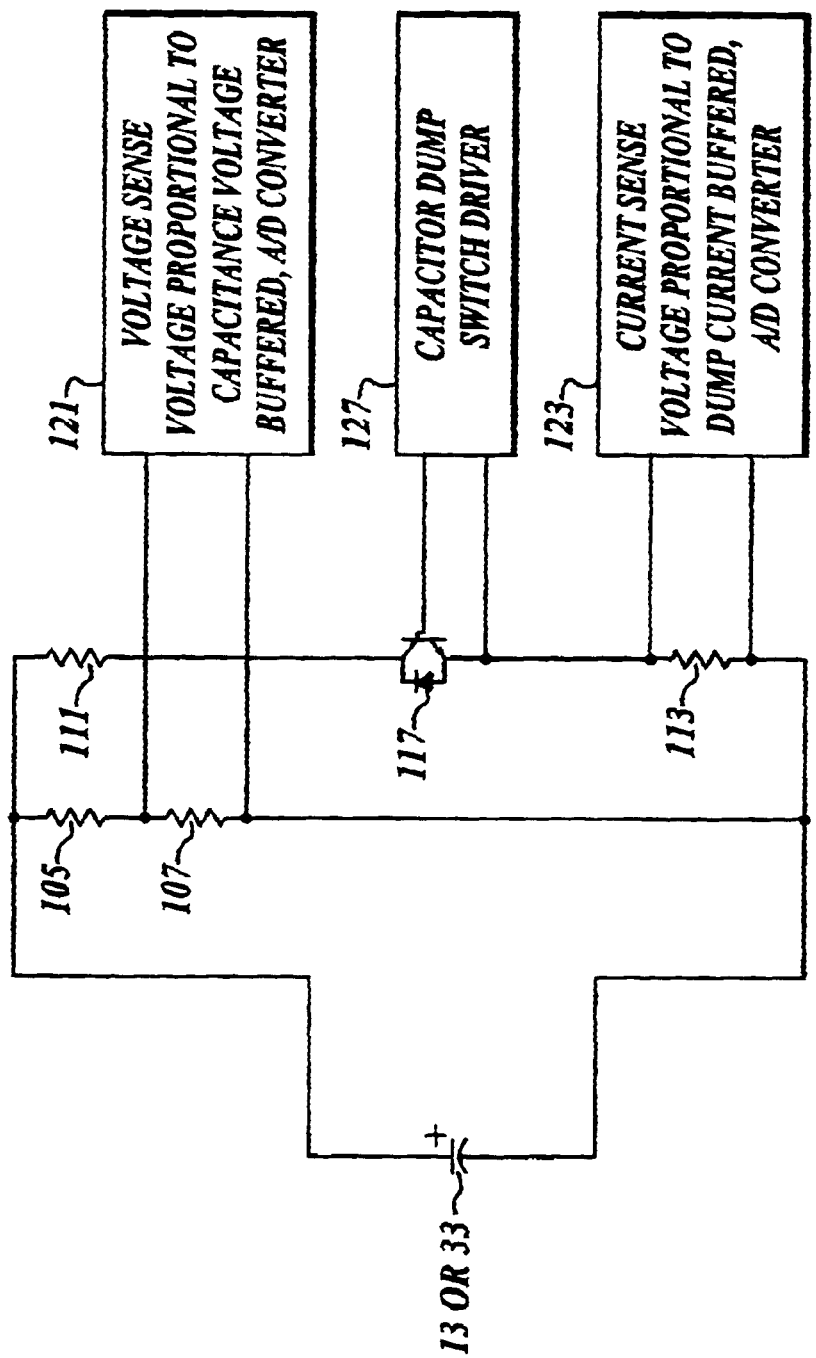
FIG. 2 is a detail schematic of the dump circuit used in the invention.

FIG. 2 portrays the second significant departure from the prior art-the dump circuit 101. The primary purpose of the dump circuit 101 is to provide an outlet for the stored charge within the capacitor when the working-coil cannot or should not receive the resulting current from discharge.

A second purpose is to measure the capacitance of the fast- and slow-capacitor banks. Capacitors 13 and 33 are variable with changes of temperature and age. As the capacitors 13 and 33 are charged and discharged, they heat internally changing their capacitance with use. Capacitors also fail, as might the connection to a capacitor.

Connected in parallel with either the fast- or slow-capacitor bank 13 and 33, the dump circuit is, principally, a resistive load for shorting across the capacitor to dissipate the power stored in the capacitor bank 13 or 33 as heat. The capacitors 13 or 33 necessary for bending of sheet metal by electromagnetic force can discharge with a voltage and current sufficient to kill. Designing the resistive load with sophistication allows the dump circuit 101 to facilitate safe discharge, but also to provide important information as to capacitance.

The resistors 105 and 107 make up a voltage divider to measure the potential difference across the terminals of the capacitor bank. The high resistive values of the two resistors 105 and 107 allow a slight current to pass through the series they comprise. The combined series resistance is large enough that the current will not burden the capacitor bank 13 or 33 or the capacitor bank charger 23 or 43.

The resistor 111 represents the dumping load. The series resistance value determines the dump speed (optimizing the RC discharge time constant), sufficient to withstand the voltage of the capacitor bank 13 and 33 and to safely dissipate its energy. The second resistor 113 is a current-sense resistor. The resistive value of resistor 113 is far lower than that of resistor 111 such that any heating of the resistor 113 will negligibly affect the derived voltage value across the series based upon the voltage drop across resistor 113.

The switch 117 may be configured in any of a number of ways. A preferred embodiment uses an Insulated Gate Bipolar Transistor (IGBT) for switching the slow-capacitor bank 13 and a vacuum relay for the fast-capacitor bank 33. While IGBT and the vacuum relay respectively represent one preferred embodiment, the design will support any switch capable of withstanding the voltage and able to switch the dump current may be used. Another embodiment would include any switch that is normally closed or able to switch on from the voltage of the capacitor bank, so that it discharges the capacitor bank when control power is removed from the circuit.

Analog-to-Digital converters 121 and 123 measure the voltages across resistors 107 and 113 respectively. In turn, these send voltage readings to the controlling and triggering instrumentation allowing for monitoring, and as a result of monitoring, the safe triggering and dumping of the fast- and slow-capacitor banks 13 and 33. To that end, the switch driver 127 is tied to the controlling instrumentation to be activated when conditions sensed require dumping the bank 13 or 33, or when used to assist in crowbarring the circuit. A plurality of combinations of switch 117 and resistor 111 might aid in adjusting the timeframe of the discharge.

Thus, monitoring the working-coil 83 current with the current sensing transformer 91 and sensor 93, isolating the gun controls 86 through optical isolation 88, and monitoring and dumping the capacitor banks 13 and 33 with dumping circuits 25 and 45 respectively assure far greater safety in the operation of an electronic dent remover.

Recalling from the earlier discussion, the triggered vacuum spark-gap 35 will operate properly at voltages representing a far smaller percentage of the self-breakdown voltage. This quality of the vacuum triggered spark-gap 35 allows test firing of the system at sub-operating voltages. The components of the power supply will operate a predictable and scaled manner at far lower charging voltages. A low voltage discharge will not stress the solid-state components, but will yield data relating to the health of the system and the inductive value of the working-coil 83. As the dump circuits enable monitoring of the charging voltage values and the discharging current corresponding to those values, the monitoring instrumentation can safely discern the capacitance of the corresponding banks through these relatively small voltage discharges.

Figure 3:
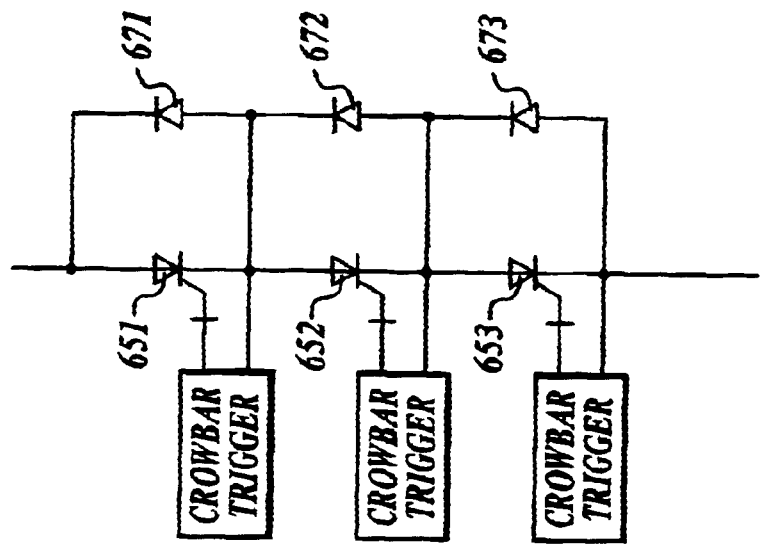
FIG. 3A is a schematic diagram of the crowbar circuit using either an optimized symmetrical blocking gate turn-off thyristor or a distributed gate thyristor.
FIG. 3B is a schematic diagram of the crowbar circuit using an insulated gate bipolar transistor (IGBT)
Figure 3:
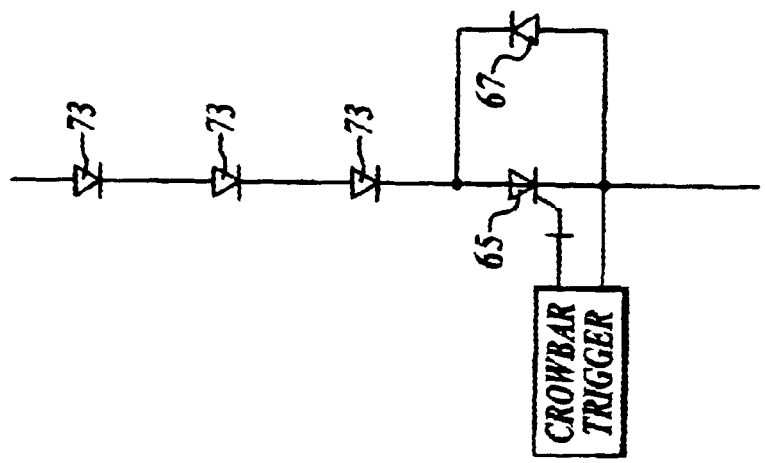

FIG. 3A portrays alternate embodiments of crowbar circuits that might take advantage of recent technologies in semiconductors. In the prior art technology, as represented by the Zieve patent, U.S. Pat. No. 5,046,345 issued to Peter B. Zieve on Sep. 10, 1991 entitled "Power Supply for Electromagnetic Proof Load Tester and Dent Remover" a crowbar circuit acts to quickly clamp the voltage across the working coil 83. Since the time of the patent, new technologies have come into existence to enhance the effect as the SCR 65 fires to effect the crowbarring of the circuit. Conventional SCRs are not optimized for applications such as those of the pulse power industry. In general, such conventional SCR applications do not require devices to withstand the very high rate of increase of forward current.

In the portrayed circuit, the substitution of either an optimized symmetrical blocking gate turn-off thyristor 65 or distributed gate thyristor 65, as a fast turn-on switch, makes the crowbar capable of switching peak currents and rates of rise of current (di/dt) in excess of 20 kA/$\mu$s per device. In contrast to the limited currents and rates of rises taught by the Zieve patent, these recent breakthroughs in switching technology present an alternative to conventional SCR technology in pulse applications. The SCR of the Zieve patent cannot rapidly begin conducting as soon as the fast capacitor bank discharges. The SCR simply cannot provide this high current and high rate of rise in the current.

Another recent leap in semiconductor technology would allow the implementation of an insulated gate bipolar transistor (IGBT) 651, 652, resistors 653 671, 672, and 673, and fast recovery epitaxial diodes (FREDs) 73. IGBTs are voltage-controlled power transistors, that have higher current densities than equivalent high-voltage power MOSFETs. As in the diagram, a triggered IGBT connected in series with a resistor comprises the unit of a gating device, for example, 651 and 671 respectively. These units are ganged in parallel appropriate to meet the current requirements of the circuit. When triggered, they handle a far greater rate of change in current flow than taught in the Zieve patent.

Figure 4:
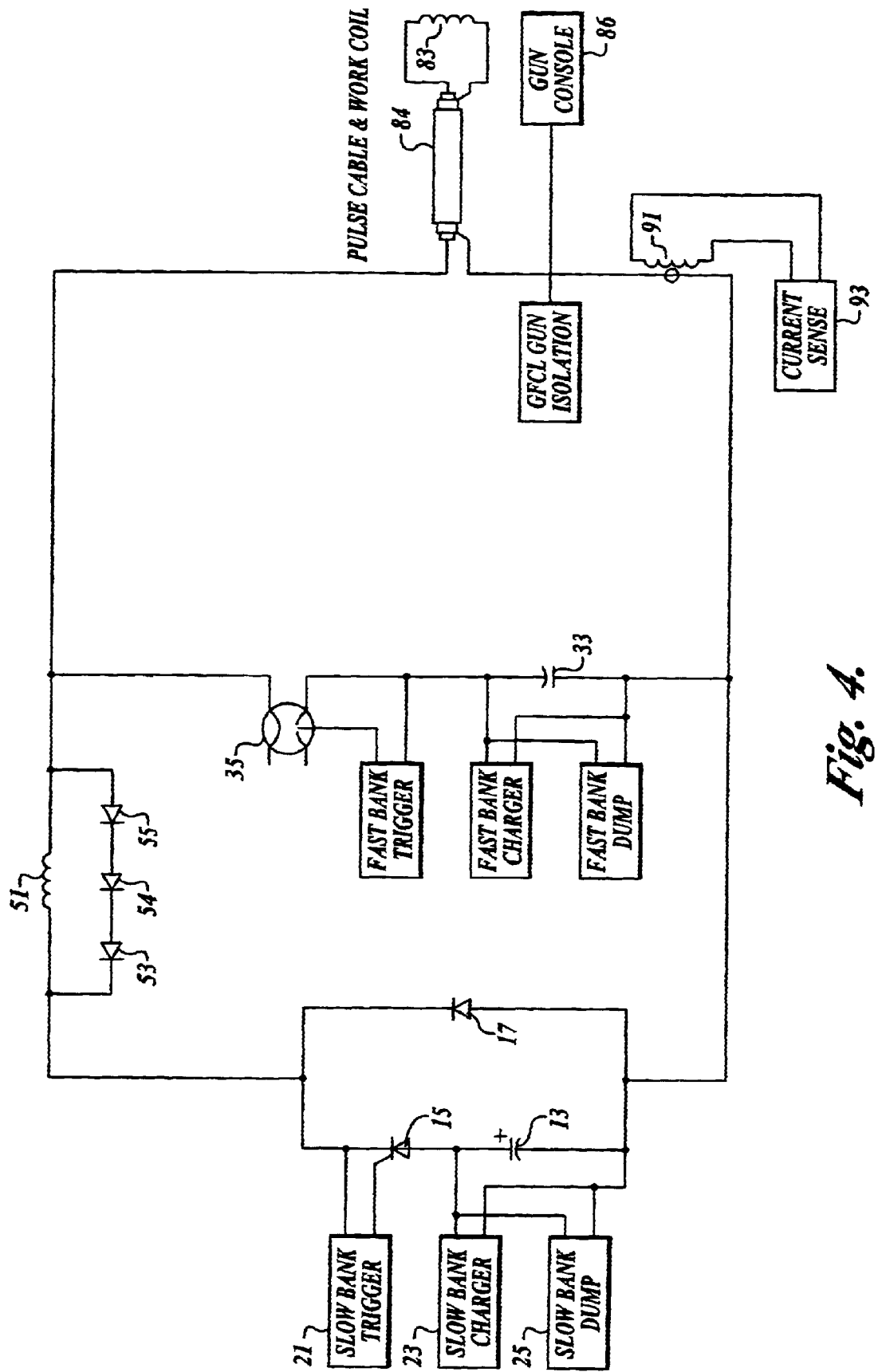
FIGS. 4 and 5 are schematic diagrams of preferred embodiments of the invention.

FIG. 4 portrays a preferred embodiment of the power supply. Lacking the crowbar circuit 61, of FIG. 1, this embodiment dissipates the energy of the inductor 51 through a series of diodes 53, 54, 55. The diodes, may be of any configuration suitable for the voltage and current requirements including FREDs. Rather than requiring the triggering impulse on the SCR 65, this circuit prevents increased energizing of the working coil 83 from the blocking inductor 51. At a time when the slow bank has or nearly has completely discharged through the blocking inductor and work coil, a triggering impulse triggers the vacuum spark-gap 35. Triggering the triggered vacuum spark-gap 35 allows the fast-capacitor bank 33 to discharge. When the fast-capacitor bank 33 discharges, it channels negative voltage to the common node of the working coil 83, blocking inductor 51, and triggered vacuum spark-gap 35. As the negative voltage decreases the current presented in the working coil 83, it increases the current in the blocking inductor 51.

In this preferred embodiment, a diode clamp circuit 75 dissipates the energy of the blocking inductor 51 providing and alternate current path. Again, the discharge of the fast-capacitor bank-33 channels negative voltage to the common node of the working coil 83, blocking inductor 51, and triggered vacuum spark-gap 35. In this embodiment, the negative voltage on fast-capacitor side of the inductor 51 results in a positive voltage across the blocking inductor 51. The diode clamp 75 provides the shunt to quickly dissipate this extra energy. The stray resistance of the blocking inductor 51 and diodes 75 determines the rate of discharge. Alternately, the engineer might place a very low resistance to moderate the discharge current.

This preferred embodiment yields several distinct advantages. Within the embodiment employing the crowbar circuit 61, the diodes 73 across the capacitor bank allow a current to continue to flow through the triggered vacuum spark gap 35. The triggered vacuum spark-gap 35 is limited in capacity by current and coulombs, so any decrease in the coulomb transfer through the vacuum gap will promote its lifetime. By eliminating the crowbar 61 of diodes 73 parallel to the fast-capacitor bank 33, this preferred embodiment eliminates a good deal of the charge transfer across the triggered vacuum spark-gap 35.

This embodiment is particularly well suited to the triggered vacuum spark-gap 35. An inherent quality of the triggered vacuum spark-gap 35 is that a minimum threshold current is necessary to keep the gap conductive. In the gas-filled spark-gap of prior art, the current will continue to conduct until the current is removed for the time necessary to allow the gas to de-ionize. Under the same conditions, the triggered vacuum spark-gap shuts down preventing further reverse charging of the fast capacitor bank.

When the fast-capacitor bank 33 completes its discharge, the primary function of the crowbar circuit 61 of the prior art was to channel the current through blocking inductor 51, by providing an alternate path for the current. Tending toward equilibrium, the inductor 51 seeks to continue to discharge its stored energy by yielding a current at a constant rate. Rather than reenergizing the working-coil 83, the discharge was shunted through the crowbar circuit 61.

Figure 5:
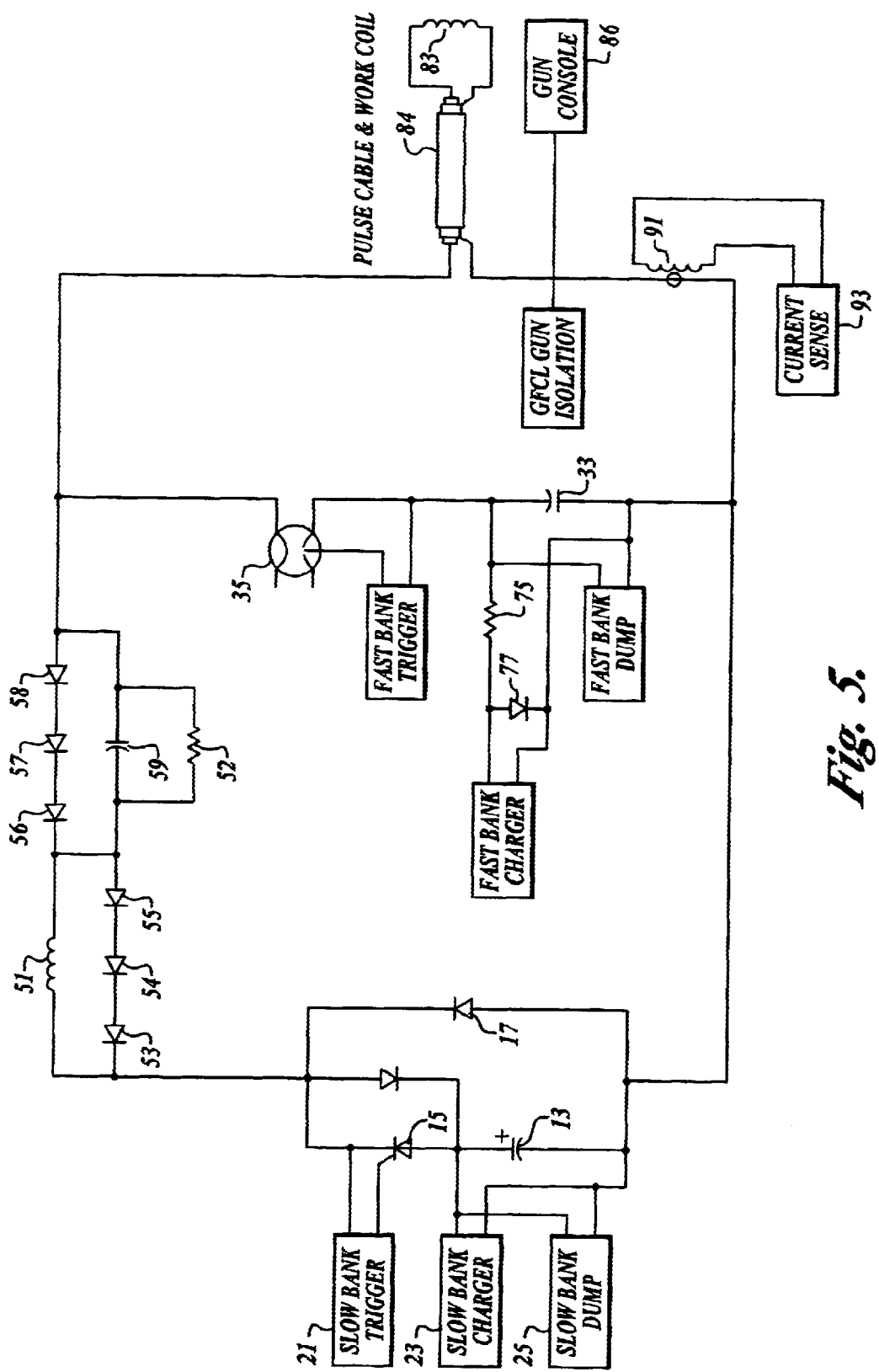

A further refinement of the circuit is portrayed in FIG. 5. As discussed in the background, a goal for improving the EDR was to prevent the failure modes that cause the EDR to make a dent instead of pulling one. By replacing the spark gap with a vacuum gap 35, the design removes one of the components that usually cause failure that, in turn, cause the forces that create large dents. Changing from the spark-gap to the vacuum-gap removes one of the failure modes resulting in dent making. This change makes dent making a less frequent occurrence.

Other components in the trigger circuit, digital circuit, software, or wiring might fail in such a way as to inadvertently trigger the vacuum gap 35 causing the same type of dent making. Judicious selection of each of the secondary components further diminishes the likelihood of false triggering of the vacuum gap 35. In addition to minimizing the likelihood of accidental firing, another approach will minimize the dent making, even in the unlikely event of this secondary failure.

In the event the fast capacitor bank fires uncontrollably without the slow bank the inventive system as portrayed in FIG. 1, that firing may create a rising current pulse that has the potential for making a dent. Quickly removing the current will lessen the damage (dent making). The embodiment portrayed in FIG. 4 will quickly divert the energy resulting in an output current waveform something like a half-sinusoid. Unfortunately diverting the current to the fast bank might result in damage to several components.

One modification; as illustrated in FIG. 5, is to direct the energy to the slow capacitor bank 13 relying upon its very large capacity. The capacitance of the slow capacitor bank 13 is so large that the current would only increase the voltage across the capacitor bank 13 slightly. Rather than clamping the voltage at zero, this modification clamps the voltage at the pre-charged level of the slow capacitor bank. The current as the capacitor bank 13 charges will decrease almost linearly at the rate determined by the slow bank voltage and the inductance of the work coil 83. To effect the clamping, the inventive circuit places the anti-parallel diode 19 across the slow bank SCR 15.

This preferred embodiment yields several distinct advantages. Within the embodiment employing the crowbar circuit 61, the diodes 77 across the capacitor bank allow a current to continue to flow through the triggered vacuum spark gap 35. The triggered vacuum spark-gap 35 is limited in capacity by current and coulombs, so any decrease in the coulomb transfer through the vacuum gap will promote its lifetime. By eliminating the crowbar 61 of diodes 77 parallel to the fast-capacitor bank 33, this preferred embodiment eliminates a good deal of the charge transfer across the triggered vacuum spark-gap 35.

Resistor 75 and diode 77 can protect and clamp the reverse voltage of the fast-bank 33 to protect the fast-bank charger. The diode 77 clamps the voltage as the resistor limits the current when the fast bank 33 is reverse charged.

While a preferred embodiment of the invention has been illustrated and described, as noted above, many changes can be made without departing from the spirit and scope of the invention. Accordingly, the scope of the invention is not limited by the disclosure of the preferred embodiment. Instead, the invention should be determined entirely by reference to the claims that follow.

What is claimed is:

1. A power supply for an electromagnetic force system, for connection to and energizing a work coil positioned adjacent a work piece, the power supply comprising:
    a slow current pulse system comprising:
        a first triggering means for discharging said slow current pulse system through the blocking inductor at a selected time;
        a first capacitor bank; and
        a dumping circuit
    a fast current pulse system, wherein the fast current pulse is of opposing polarity to the slow current pulse comprising:
        a second triggering means for discharging the fast current pulse system through said coil such that the current through the coil decreases rapidly and creates a pulse of tension force on the work piece; and
        a second capacitor bank; and
    a block inductor.

2. A power supply for an electromagnetic force system, for connection to and energizing a work coil positioned adjacent a work piece, the power supply comprising:
    a slow current pulse system comprising:
        a first triggering means for discharging said slow current pulse system through the blocking inductor at a selected time; and a first capacitor bank;

a fast current pulse system, wherein the fast current pulse is of opposing polarity to the slow current pulse comprising:
  a second triggering means for discharging the fast current pulse system through said coil such that the current through the coil decreases rapidly and creates a pulse of tension force on the work piece;
  a second capacitor bank; and
  a triggered crowbar across the second triggering means and the second capacitor bank, the triggered crowbar including:
    a third triggering means including a distributed gate thyristor; and a blocking inductor.

3. A power supply for an electromagnetic force system, for connection to and energizing a work coil positioned adjacent a work piece, the power supply comprising:
a slow current pulse system comprising:
  a first triggering means for discharging said slow current pulse system through the blocking inductor at a selected time; and
  a first capacitor bank;
a fast current pulse system, wherein the fast current pulse is of opposing polarity to the slow current pulse comprising:
  a second triggering means for discharging the fast current pulse system through said coil such that the current through the coil decreases rapidly and creates a pulse of tension force on the work piece;
  a second capacitor bank; and
  a triggered crowbar across the second triggering means and the second capacitor bank, the triggered crowbar including:
    a third triggering means including at least one transistor in parallel; and
a blocking inductor.

4. A power supply for an electromagnetic force system, for connection to and energizing a work coil positioned adjacent a work piece, the power supply comprising:
a slow current pulse system comprising:
  a first triggering means for discharging said slow current pulse system through the blocking inductor at a selected time including; and
  a first capacitor bank;
a fast current pulse system, wherein the fast current pulse is of opposing polarity to the slow current pulse comprising:
  a second capacitor bank; and
  a second triggering means for discharging the fast current pulse system through said coil such that the current through the coil decreases rapidly and creates a pulse of tension force on the work piece including a triggered vacuum spark-gap in series with the second capacitor bank; and
a blocking inductor.

5. The power supply of claim 1 wherein the fast pulse system comprises a dumping circuit.

6. A power supply for an electromagnetic force system, for connection to and energizing a work coil positioned adjacent a work piece, the power supply comprising:
a slow current pulse system comprising:
  a first triggering means for discharging said slow current pulse system through the blocking inductor at a selected time; and
  a first capacitor bank;
a fast current pulse system, wherein the fast current pulse is of opposing polarity to the slow current pulse comprising:
  a second triggering means for discharging the fast current pulse system through said coil such that the current through the coil decreases rapidly and creates a pulse of tension force on the work piece
  a second capacitor bank; and
  a fast bank charger in parallel to the second capacitor bank and
a blocking inductor.

7. The power supply of claim 6 wherein the fast pulse system comprises a third resistive load in series with the fast bank charger.

8. The power supply of claim 6 wherein the fast pulse system comprises a fifth fly-back diode in parallel across the fast bank charger.

* * * * *